US 6,737,619 B2

(12) United States Patent
Seghatol et al.

(10) Patent No.: US 6,737,619 B2
(45) Date of Patent: *May 18, 2004

(54) MICROWAVE POLYMERIZATION SYSTEM FOR DENTISTRY

(76) Inventors: Marc Seghatol, 750 Monpellier Street 216, St. Laurent, Quebec (CA), H4L 5A7; Jean-Pierre Durand, 1820 Laurier, St. Catherine, Quebec (CA), J0L 1E0

(*) Notice: Subject to any disclaimer, the term of this patent is extended or adjusted under 35 U.S.C. 154(b) by 0 days.

This patent is subject to a terminal disclaimer.

(21) Appl. No.: 10/166,569

(22) Filed: Jun. 10, 2002

(65) Prior Publication Data

US 2003/0057203 A1 Mar. 27, 2003

Related U.S. Application Data

(63) Continuation of application No. 09/399,997, filed on Sep. 20, 1999, now Pat. No. 6,441,354.

(30) Foreign Application Priority Data

Sep. 18, 1998 (CA) .............................................. 2246663

(51) Int. Cl.[7] .............................. H05B 6/68; H05B 6/80
(52) U.S. Cl. ........................ 219/679; 219/709; 219/748; 264/402; 425/174.8 E; 522/1
(58) Field of Search ................................. 219/679, 702, 219/704, 705, 696, 746, 709, 748, 750, 686; 422/21; 264/402, 405, 432; 425/174.8 R, 174.8 E; 522/1; 433/167

(56) References Cited

U.S. PATENT DOCUMENTS

| 4,527,560 A | 7/1985 | Masreliez |
|---|---|---|
| 4,873,269 A | 10/1989 | Nakazato |
| 4,971,735 A | 11/1990 | Uebayashi |
| 5,147,903 A | 9/1992 | Podszun et al. |
| 5,151,279 A | 9/1992 | Kimura |

(List continued on next page.)

FOREIGN PATENT DOCUMENTS

| CA | 2120880 | | 10/1995 |
|---|---|---|---|
| CA | 2148536 | | 11/1995 |
| DE | 41 02 129 | * | 7/1992 |
| EP | 0 193 514 B1 | | 8/1990 |
| EP | 0 687 451 A2 | | 12/1995 |
| JP | 7031632 A | | 2/1995 |

OTHER PUBLICATIONS

Feilzer AJ et al., "Curing contraction of composites and glass–ionomer cements," *Journal of Prosthetic Dentistry*, vol. 59, pp. 297–300 (1988).

Ferracane JL et al., "Wear and marginal breakdown of composite with various degrees of cure," *J Dent. Res.*, vol. 76, No. 8, pp. 1508–1516 (1997).

(List continued on next page.)

*Primary Examiner*—Philip H. Leung
(74) *Attorney, Agent, or Firm*—Patterson, Thuente, Skaar & Christensen, P.A.

(57) ABSTRACT

A microwave polymerization system for dentistry utilizes specifically controlled microwave energy to cure polymer materials so as to produce dental prosthetics, such as dentures, bridges and crowns, that are made in an extra-oral setting such as a dental laboratory or dental office, and to create dental composites for fillings and veneers that are used in an intra-oral setting directly in the patient's mouth. Unlike the microwave energy delivered by commercial microwave ovens, the system utilizes metered and controlled microwave energy that is preferably continuous and voltage controlled, and regulates the application of this microwave energy by use of various feedback and control mechanisms. The metered and controlled microwave energy enables a higher degree of conversion of monomers into polymer chains in the polymerization process, thereby enhancing the physical and biocompatibility characteristics of both dental prosthetics and dental composites made from polymers.

11 Claims, 5 Drawing Sheets

U.S. PATENT DOCUMENTS

| | | | |
|---|---|---|---|
| 5,175,008 | A | 12/1992 | Ueno |
| 5,218,070 | A | 6/1993 | Blackwell |
| 5,302,104 | A | 4/1994 | Ueda |
| 5,324,186 | A | 6/1994 | Bakanowski |
| 5,421,727 | A | 6/1995 | Stevens et al. |
| 5,502,087 | A | 3/1996 | Tateosian et al. |
| 5,632,955 | A | 5/1997 | Gabbai |
| 5,645,748 | A | 7/1997 | Schiffmann et al. |
| 5,770,143 | A | 6/1998 | Hawley et al. |
| 5,893,713 | A | 4/1999 | Garman et al. |
| 6,441,354 | B1 * | 8/2002 | Seghatol et al. ............ 219/679 |

OTHER PUBLICATIONS

Hayden WJ, "Flexure strength of microwave–cured denture baseplates", *General Dentistry*, vol. 343, pp. 367 (1986).

Al Doori D et al. "A comparison of denture base acrylic resins polymerised by microwave irradiation and by conventional water bath curing systems," *Dental Materials*, vol. 4, pp. 25–32 (1988).

Geerts G et al., "A comparison of the bond strengths of microwave and water bathcured denture materials," *The Journal of Prosthetic Dentistry*, vol. 66, No. 3, pp. 403–407 (Sep. 1991).

Turck MD et al, "Microwave processing for dentures, relines, repairs and rebases," *The Journal of Prosthetic Dentistry*, vol. 69, No. 3, pp. 340–343 (1993).

Wallace PW et al., "Dimensional accuracy of denture resin cured by microwave energy," *The Journal of Prosthetic Dentistry*, vol. 68, pp. 634–640 (1992).

Salim S. et al. "The dimensional accuracy of rectangular acrylic resin specimens cured by three denture base processing methods," *The Journal of Prosthetic Dentistry*, vol. 67, pp. 879–885 (1992).

Ferracane JL, "Elution of leachable components from composites," *Journal of Oral Rehabilitaion*, vol. 21, pp. 441–452 (1994).

Hume WR et al., "Bioavailability of components of resin–based materials which are applied to teeth," *Crit. Rev. Oral Biol. Med.*, vol. 7, No. 2, pp. 172–179 (1996).

Alkhatib MB, et al. "Comparison of microwave–polymerized denture base resins," *The International Journal of Prothodontics*, vol. 3, No. 2, pp. 249–255 (1990).

Urabe H. et al. in "Influence of polymerization initiator for base monomer on microwave curing of composite resin inlays," *Journal of Oral Rehabilitation*, vol. 26, pp. 442–446 (1999).

"The Prosthoflex automated injection system from ATP Industries, Inc." *Dental Lab Products*, Sep./Oct. 1995, pp. 14.

N. Hoshi et al in "Application of Microwaves and Millimeter Waves for the Characterization of Teeth for Dental Diagnosis and Treatment," *IEEE Transactions on Microwave Theory and Techniques*, Jun. 1998.

* cited by examiner

MICROWAVE POLYMERIZATION SYSTEM FOR DENTISTRY

RELATED APPLICATION

The present invention is a continuation of co-pending U.S. patent application Ser. No. 09/399,997 entitled MICROWAVE POLYMERIZATION SYSTEM FOR DENTISTRY, filed Sep. 20, 1999 now U.S. Pat. No. 6,441,354, which claims priority to PCT Application No. PCT/US99/20960, filed Sep. 17, 1999, which claims priority to Canadian Patent No. 2,246,663, filed Sep. 18, 1998, the contents of all of which are hereby incorporated by reference.

FIELD OF THE INVENTION

The present invention relates generally to the field of dentistry. More specifically, the present invention relates to a microwave polymerization system for dentistry that utilizes specifically controlled microwave energy to cure polymer materials so as to produce dental prosthetics and dental composites having improved physical characteristics.

BACKGROUND OF THE INVENTION

The use of polymer materials in the dental arts for the restoration of lost or damaged teeth is well known. Such uses fall into two general categories: (i) the use of polymer materials to produce dental prosthetics, such as dentures, bridges and crowns, that are either permanent or removable articles, and (ii) the use of polymer materials to create dental composites for fillings to repair teeth instead of using conventional amalgam fillings or as veneers to refinish tooth enamel surfaces. The first category of dental articles, dental prosthetics, are created outside of the patient (i.e., extra-oral), typically by making an impression of what the desired article should look like and then molding the article to match the impression. The second category of dental articles, dental composites, are created directly in the patient's mouth (i.e., intra-oral) as fillings or veneers to repair or resurface teeth. Regardless of which category is being considered, dental articles made of polymer materials must have adequate strength, durability, and dimensional stability and must also be biocompatible and chemically inert. It is also important to be able to process each type of dental article rapidly, conveniently, safely and economically.

An example of a dental prosthetic in the first category of dental articles that is created using polymer materials is a removable denture. Most commercial dentures are created using a paste or resin matrix formed of various polymers, co-polymers and monomers (typically methyl methacrylate), as well as certain cross-linking agents, initiators, accelerators and other additives. This resin matrix is formed into a plaster mold and is then hardened or cured by applying energy in the form of heat. Typically, the plaster mold containing the uncured denture is prepared in a dental laboratory based on an impression taken by the dentist. To cure the resin matrix, the plaster mold is placed into a flask that is then put in a thermal water-bath for up to 8 hours. This conventional process of curing a denture takes such a long time because both the plaster molds and the polymers in the resin matrix are relatively poor thermal conductors and are heated only from the outside via the thermal water-bath. The conventional process can also result in large numbers of voids and significant shrinkage during curing due to uneven thermal conduction and non-uniform polymerization of the resin matrix. These problems are discussed in Feilzer A. J. et al., "Curing contraction of composites and glass-ionomer cements," *Journal of Prosthetic Dentistry*, Vol. 59, pp. 297–300 (1988); and Ferracane J. L. et al., "Wear and marginal breakdown of composite with various degrees of cure," *J Dent. Res.*, Vol. 76, No. 8, pp. 1508–16 (1997). The lack of completely uniform polymerization of the denture also leaves residual monomers that are toxic and can act as irritants to oral tissues and compromise the physical characteristics of the denture.

In an effort to overcome the long cure times associated with the conventional thermal water-bath technique, a technique of using commercial microwave ovens to heat and cure polymer resins to form dental prosthetics has been developed. In the conventional thermal curing method for polymer dental articles, a temperature differential is required to force heat by conduction from the surface of the flask and mold to the center of the article. Because the heat penetrates from the outside to the internal portions of the material by thermal conduction, overheating and degrading polymers can occur at the outer surface of the article. When microwaves are used to initiate the thermal curing processing, it is possible for the article to be heated uniformly as the electromagnetic radiation instantaneously penetrates deeply and heating occurs throughout all three dimensions of the irradiated article. The main advantages provided by microwave energy include a rapid internal heating independent of the heat flow through the surface, as well as minimal thermal lag and thermal gradients throughout the interior of the article, which results in a more homogeneous curing of the article with a higher degree of conversion of monomers into polymer chains.

Comparisons of these two techniques can be found in Hayden W. J., "Flexure strength of microwave-cured denture baseplates", *General Dentistry*, Vol. 343, pp. 367 (1986); Al Doori D et al. "A comparison of denture base acrylic resins polymerized by microwave irradiation and by conventional water bath curing systems," *Dental Materials*, Vol. 4, pp. 25–32 (1988); and Geerts G. et al., "A comparison of the bond strengths of microwave and water bath-cured denture materials," *The Journal of Prosthetic Dentistry*, Vol. 66, No. 3, pp. 403–07 (Sep. 1991). Various types of flasks and molding equipment that can be used in conjunction with a commercial microwave oven for processing and curing dental articles made of polymers have been developed as described, for example, in U.S. Pat. Nos. 4,971,735, 5,151,279, 5,324,186 and 5,510,411, European Patent No. 0 687 451 A2, and Japanese Patent No. JP7031632A. The repair of dentures and related articles using microwave processing is also described in Turck M. D. et al, "Microwave processing for dentures, relines, repairs and rebases," *The Journal of Prosthetic Dentistry*, Vol. 69, No. 3, pp. 340–43 (1993). Generally, dentures cured by commercial microwave ovens have improved mechanical properties, and often have better adaptation than those cured by the water-bath method. The primary advantage of microwave curing, however, is the reduced processing times which can be shortened from 8 hours or more to as little as a few minutes.

While the use of commercial microwave ovens to cure dental prosthetics solves some of the problems of conventional thermal water-bath cured prosthetics, dental prosthetics processed in this manner can be less than satisfactory in terms of their physical and biocompatibility characteristics because varying degrees of cure, micro-shrinkage and porosities are still present. Any large degree of micro-shrinkage or porosities in the polymers of dental prosthetics cured using conventional microwave ovens will lead to fitting inaccuracy and unreliability. These problems are discussed in Wallace P. W. et al., "Dimensional accuracy of denture resin cured by microwave energy," *The Journal of Prosthetic Dentistry*, Vol. 68, pp. 634–40 (1992); and Salim S. et al. "The dimensional accuracy of rectangular acrylic resin specimens cured by three denture base processing methods," *The Journal of Prosthetic Dentistry*, Vol. 67, pp. 879–85 (1992).

It understood in the dental arts that micro-shrinkage is primarily due to the resin matrix. The physical and mechanical properties of a polymer material, such as hardness, stiffness and abrasion resistance and strength, are highly influenced by the arrangement of the resin matrix when the fillers and coupling agents are fixed during the curing process. Micro-shrinkage results from the shorter distance between atoms in the resin matrix after polymerization than before polymerization. The monomers in the resin matrix are located at Van der Waals distance, which change to a covalent bond distance once the resin matrix is polymerized. If all of the monomers in the resin matrix are not converted into polymer chains during the polymerization curing process, then this change in distance can induce mechanical stresses in the form of micro-shrinkage in those areas where there was not complete conversion of the monomers into polymers. Commercial resin matrices are found to undergo volume shrinkage of as much as 7% with most resin matrices shrinking 2–3%. This kind of micro-shrinkage causes volumetric dimensional change that can result in poor fitting of the dental prosthetic to oral tissues and can build up mechanical stress in the dental prosthetic that can lead to premature mechanical failure. A discussion of some of these issues can be found in D. Bogdal, "Application of Diol Dimethacrylates in Dental Composites and Their Influence on Polymerization Shrinkage," *J. Appl. Polym. Sci.*, Vol. 66, pp. 2333–2337 (1997), and D. Bogdal et al., "The Determination of Polymerization Shrinkage of Materials for Conservative Dentistry," *Polimery*, Vol. 41, pp. 469 (1996).

Another problem caused by the residual monomers not being converted into polymer chains during the polymerization curing process is the leaching of any unbound monomers or additives out of the article. The leaching has an impact on both the structural stability and biocompatibility. The residual monomers can leach into salivary fluids which then irritates any mouth tissues in contact with these contaminated fluids; or the residual monomers can diffuse directly into the dentin and pulp of teeth adjacent to the dental prosthetic. These problems are described in Ferracane J. L., "Elution of leachable components from composites," *Journal of Oral Rehabilitation*, Vol. 21, pp. 441–52 (1994); and Hume W. R. et al., "Bioavailability of components of resin-based materials which are applied to teeth," *Crit. Rev. Oral Biol. Med.*, Vol. 7, No. 2, pp. 172–79 (1996).

The primary solutions to these problems have focused on increasing the degree of polymerization and cross-linking of all of the monomers in the resin matrix by changing the formulation of the resin matrix. Improvements in resin formulation involve, for example, the introduction of spiro orthocarbonates and stereoisomers. U.S. Pat. No. 5,502,087 describes various polymer-based resins that are designed to improve the physical characteristics of thermal water-bath cured resin matrices or light-activated resin matrices. U.S. Pat. No. 5,147,903 describes polymer materials that exhibit desired degrees of swelling and cross-linking for light-activated resin matrices. Examples of polymer resin matrices that are specifically formulated to utilize microwave energy supplied by a commercial microwave oven for the thermal polymerization of the polymers into dental articles are shown in U.S. Pat. Nos. 4,873,269, and 5,218,070, and Canadian Patent No. 2,148,436. The impact of the role played by the polymer initiator in a microwave cured resin matrix has been evaluated by Urabe H. et al. in "Influence of polymerization initiator for base monomer on microwave curing of composite resin inlays," *Journal of Oral Rehabilitation*, Vol. 26, pp. 442–46 (1999).

Another solution to these problems is also described in Canadian Patent No. 2,148,436 in which the resin matrix in the mold is compressed by a mechanical ram that injects additional uncured polymer components into the mold while the mold and flask are being cured inside a commercial microwave oven. The mechanical ram slowly forces some of the uncured polymer material contained in an injection cartridge through a passageway or sprue into the mold. The addition of polymer material applied under mechanical compression while it is still fluid is another way of reducing problems related to the polymerization shrinkage and porosity. U.S. Pat. Nos. 5,175,008 and 5,302,104 and Canadian Patent No. 2,120,880 describe various solutions for providing similar types of mechanical compression in the context of molding dental prosthetics without using microwave energy to cure the resin matrix.

There had been relatively little research, however, into the potential impact of the microwave energy itself on the polymerization process. The most common use of microwave energy to cure dental prosthetics actually involves a two-stage process where, as described in U.S. Pat. No. 4,971,735, the microwave energy first quickly heats water in or around the flask or humidity in a moist mold, with the superheated water vapor then thermally conducting the generated heat to the resin matrix. Due to the superheated nature of this process, cure times can be dramatically reduced. Moreover, because the microwave energy is primarily being absorbed by water as the intermediary thermal agent, this process lends itself very well to the use of commercial microwave ovens operating at full power settings where the primary objective is to heat the water, and not necessarily the resin matrix. This is advantageous because commercial microwave ovens are controlled by cycling the microwave generator, known as a magnetron, on and off to provide an average output power that corresponds to the percentage of the duty cycle. For example, a 50% duty cycle operates the magnetron on 50% of the time and produces a power output in terms of watts of energy produced by the oven that would be one-half of the maximum power output of the oven.

The other mechanism by which microwave energy can be used to cure dental prosthetics involves a single stage process where the microwave energy is directly absorbed by the molecules of the resin matrix without any substantial assistance of an intermediary thermal transfer agent, such as water vapor. In this case, the microwave energy essentially vibrates the resin molecules in a complicated process that is dependent upon the specific nature of the chemical composition of the resin matrix. It has been found that where water vapor in the form of humidity is present in the process, the actual polymerization of the resin matrix will occur as a result of a combination of thermal conduction from water vapor and internal microwave energy transfer.

Unfortunately, the high temperatures generated in the targeted article by microwave heating with available commercial microwave ovens set to manufacturers' recommendations (e.g., 3 minutes at 550W at 100% duty cycle for a G. C. Acron dental microwave oven) tend to result in the thermal degradation of, and porosity formation in, many thermosetting polymer materials since high temperatures (above 150° C.) are often produced during these curing processes. In addition, hot and cold spots are often found within commercial microwave ovens that tend to create thermal gradients corresponding to these variations in microwave energy internal to the article being cured. The problems caused by these hot and cold spots can be compounded by the superheated nature of the water vapor, which effectively amplifies any uneven distribution of the thermal energy to the resin matrix.

What little research has been done on the effect of microwave energy on the polymerization process has generally focused on the duty cycle used for the microwave curing process. The impact on porosity of denture material cured using lower wattage, longer duration microwave cure times (i.e., a lower duty cycle for a longer time) versus higher wattage, shorter duration microwave cure times (i.e., a higher duty cycle for a shorter time) is compared in Alkhatib M. B., et al. "Comparison of microwave-polymerized denture base resins," *The International Journal of Prothodontics*, Vol. 3, No. 2, pp. 249–55 (1990). European Patent No. 0 193 514 B1 describes a microwave processing system for dental prosthetics that has a magnetron, a waveguide, a surface radiating antenna, a flask, and a temperature sensor that is inserted in the flask and connected to a regulating processor. The regulating processor limits the temperature in the flask as measured by the temperature sensor by turning on and off the magnetron based on frequency modulation of the duty cycle. Although not used for polymerization of dental articles, U.S. Pat. No. 5,645,748 does describe a microwave system for sterilization that controls duty cycle of a microwave oven for the purpose of minimizing arcing caused by metallic surgical or dental instruments.

Any increase in the degree of conversion of monomers into polymer chains in the polymerization process will result in improved mechanical properties and biocompatibility of microwave cured dental prosthetics. While existing solutions utilizing improved resin compositions and mechanical compression during the curing process with a commercial microwave oven have resulted in many improvements over the conventional thermal water-bath method of producing dental prosthetics, it would be desirable to further improve the uniformity and the degree of conversion of monomers into polymer chains in the polymerization process and further compensate for volumetric shrinkage during the polymerization process in order to produce even better dental prosthetics.

With respect to the second category of dental articles created using polymer materials, dental composites formed of polymer matrix-composites are increasingly being used as an alternative to mercury-containing dental amalgam for aesthetic and restorative dental materials. These kinds of polymer matrix-composites are usually photo polymerizable in that they are cured using some kind of light instead of heat. Generally, the polymer matrix-composite is based on a photo polymerizable polyfunctional methacrylate compound that can be used alone or as mixture with monomethacrylates, light sensitive cure initiators pigments and fillers in a mixture with various comonomers such as triethyleneglycol dimethacrylate. Although the half-life of these polymer matrix-composites cured by light is on the order of 5–8 years and, therefore, they tend to wear out earlier than conventional dental amalgams, the enhanced biofunctionality and more pleasing aesthetic qualities of these polymer matrix-composites have gained favor over conventional dental amalgams.

The main deficiencies of polymer composite resins used as dental composites are surface degradation that leads to inadequate wear resistance, polymerization shrinkage and a lack of density. In addition to the problems previously described for dental prosthetics, micro-shrinkage of polymer dental composites produces interfacial gaps on the surface of the composites, which can results in microleakage through the dental composite. The long-term consequence of such microleakage can be bacterial penetration into the tooth that can cause a variety of adverse reactions in the tooth such as pulp damage, tooth sensitivity, possible pulpal death and loss of adhesion of the dental composite.

Just as with polymer dental prosthetics, improving the degree of polymerization of polymer matrix-composites is generally considered to be one way of improving their physical and biofunctionality characteristics of polymer dental composites as this would lead to stronger dental composites that are less susceptible to degradation, wear and fracture. It would also lead to improved biocompatibility, since there would be reduced amounts of uncured monomer that could act as a biohazard.

Unlike polymer dental prosthetics, however, the curing of polymer matrix-composites by application of thermal energy generally has not been used to date. Obviously, in the case of the conventional thermal water-bath process, it would be impractical to require a patient to remain at the dentist's office for up to 8 hours with their mouth open and with a tooth immersed in a hot water bath in order to set a thermally polymerizable matrix-composite. It is also not possible to place a patient's mouth into a commercial microwave oven to set a thermally polymerizable matrix-composite.

While there are numerous hand-held medical catheter devices that utilize radio frequency and microwave energy to perform ablations and similar heating operations, for example, in the vascular system of a patient, there have been relatively few uses of thermal or electrical energy applied to hand-held dental tools for intra-oral applications. There have been a few hand-held dental probes that utilize an electrically resistive heated tip for diagnosis of dental decay or for melting a sealing material in an intra-oral context as described, for example, in U.S. Pat. Nos. 4,527,560 and 5,893,713. U.S. Pat. No. 5,421,727 describes the use of radio frequency/microwave energy as part of a hand-held endodontic root canal device to raise the temperature of the adjacent tooth, thereby tending to disinfect the tooth during the root canal procedure as a result of the increased temperature.

The extra-oral use of microwave energy for the purpose of characterizing dental decay in extracted teeth has been described by N. Hoshi et al in "Application of Microwaves and Millimeter Waves for the Characterization of Teeth for Dental Diagnosis and Treatment," *IEEE Transactions on Microwave Theory and Techniques*, June 1998, Vol. 46, No. 6, pp. 834–38. This study confirmed the higher absorbency behavior of carious lesions in extracted teeth when irradiated by microwave energy as compared to the lower absorbency of such microwave energy by healthy enamel and dentin.

While existing photo polymerizable dental composites have enjoyed success as compared to conventional dental amalgams for dental fillings and veneers, it would be desirable to further improve the uniformity and degree of conversion of monomers into polymer chains in the polymerization process in order to produce even better dental composites.

SUMMARY OF THE INVENTION

The present invention is a microwave polymerization system for dentistry that utilizes specifically controlled microwave energy to cure polymer materials so as to produce dental prosthetics and dental composites. Unlike the microwave energy delivered by commercial microwave ovens which is controlled by pulsing a maximum output power on and off at a given duty cycle, the present invention utilizes metered and controlled microwave energy that is preferably continuous and voltage controlled, and regulates the application of this microwave energy by use of various feedback mechanisms. The metered and controlled microwave energy enables a higher degree of conversion and cross-linking of monomers into polymer chains in the polymerization process, thereby enhancing the physical and biocompatibility characteristics of both dental prosthetics and dental composites made in accordance with the present invention. In an extra-oral embodiment, gaseous pressure is applied to the resin matrix during the polymerization process to further enhance the polymerization process. In an intra-oral embodiment, the polymerization process can be accomplished with less overall energy and with composite-matrices that maximally absorb the microwave energy so as to reduce heating of adjacent tissue.

In one embodiment, a microwave oven is designed to apply continuous microwave energy in accordance with the extra-oral embodiment of the present invention for use in producing dental prosthetics at either a dental laboratory or a dental office. Microwave energy of between 1 GHz to 100 GHz, and preferably about 2.45 GHz, is continuously generated in the microwave oven in response to precisely controlled voltages of between 25 V and 110 V, depending upon the desired curing time and the particular composition of the resin matrix to be cured. A flask for use in the microwave oven is preferably provided with a mechanism to rotate the flask and with quick disconnect rotatable couplers for both liquid polymer insertion and gas pressurization while the article is rotating and undergoing the microwave curing process. The insertion of additional polymer and the gas pressurization system are utilized to maintain controlled gaseous pressure on the polymer material during the curing process to increase the density of the cured dental prosthetic and to compensate for micro-shrinkage that may occur during polymerization. Pressurization rates depend upon the strength characteristics of the polymer composition being used and preferably range between 10 psi to 125 psi with optimal ranges of between 12–35 psi. The flask may be equipped with an internal membrane to compress and adapt the pasty curable resin matrix onto the mold and with a vacuum forming system to draw the curable resin matrix into the mold and assist in maintaining the resin matrix in the mold during the curing process. In one embodiment, a cartridge is provided with quick disconnect couplers between the gas pressurization system and a sprue connected to the flask to permit filling of the mold with the curable resin matrix stored in the cartridge. Optionally, the microwave oven may be provided with features that also allow it to be used to sterilize dental prosthetics and other objects in a dental office or dental laboratory.

BRIEF DESCRIPTION OF THE DRAWINGS

FIG. 5 is a top cut-away view of the flask shown in FIG. 3 showing a mold in position within the flask.

DETAILED DESCRIPTION OF THE PREFERRED EMBODIMENT

Figure 1:
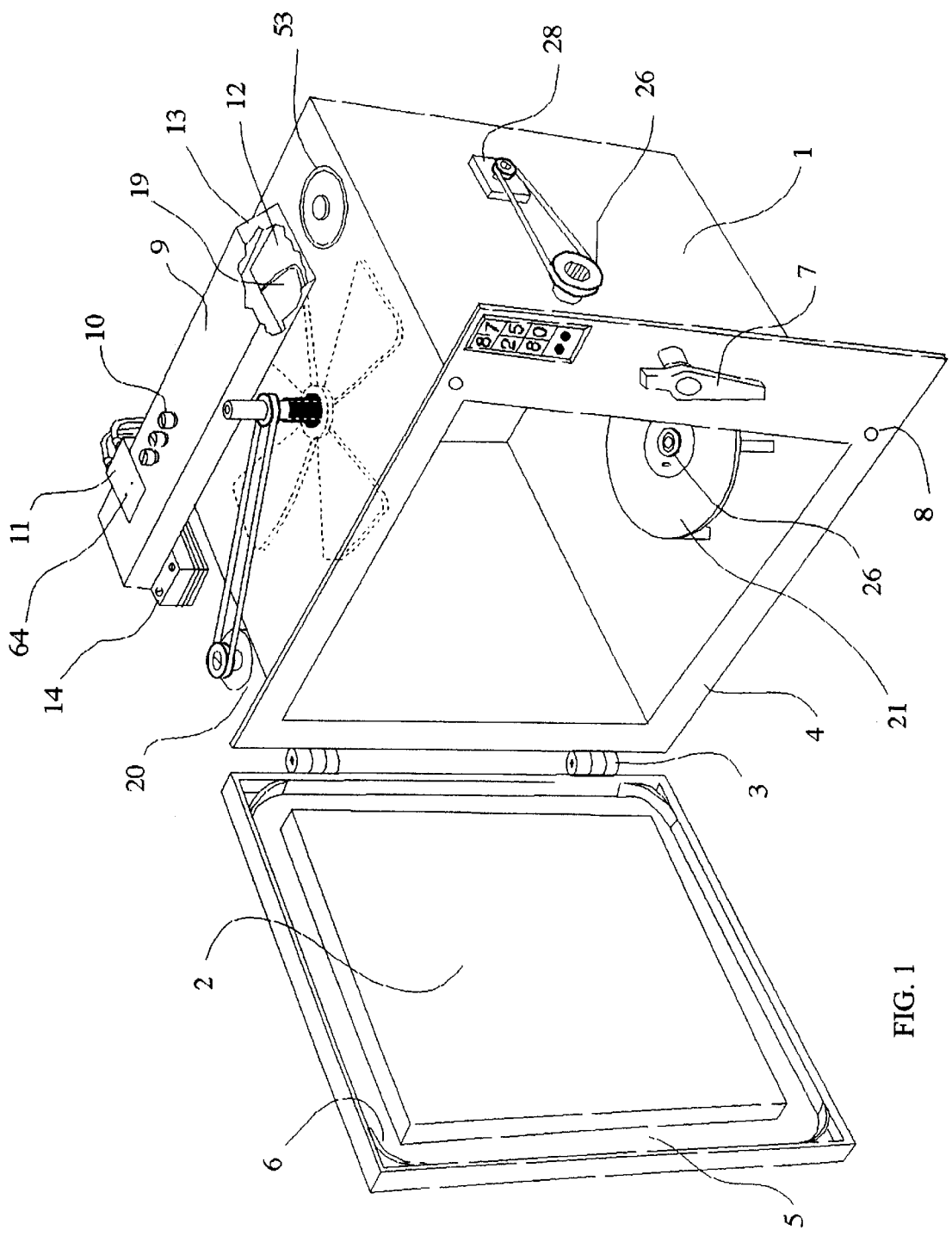
FIG. 1 is an isometric view of a microwave oven embodiment of the present invention.

Referring now to the various figures, a detailed description of the preferred embodiment of the present invention will be presented. To understand the details on which the preferred embodiment is based, it is helpful to understand how microwave energy is generated and absorbed. The microwave energy absorbed by a given dental material is governed by the following equation:

$$P = 2\pi f E^2 \epsilon' \tan \delta$$

where:

P=Power density (w/m$^3$)

f=frequency

E=electrical field strength (rms)

$\epsilon'$=dielectric constant of the dental material tan $\delta$=dielectric loss factor.

This equation shows that in order to determine the microwave energy in terms of the incident microwave power level absorbed by a dental article, both the applied electric field strength and the dielectric material characteristics must be known. One of the difficulties in properly evaluating this equation is that when a curable dielectric resinous material is polymerized, its microwave absorption is drastically reduced because the dielectric constant of the material changes as a result of the polymerization process.

In commercial microwave ovens, microwave power reduction and control is accomplished by pulsing the full power generated by the microwave generator on and off over some duty cycle or time base, wherein a duty cycle or time base is defined to be the amount of time from beginning the pulsing of power to the time pulsing is completed. For example, in an 800 watt oven, it is possible to achieve a relative average output of 400 watts, or 50% power, by pulsing the full 800 watts on and off, assuming the pulse width is equal to half the pulse period. Even though an average output of 400 watts can be accomplished in this manner, for each on-time of the duty cycle, the full 800 watts is actually on and applied inside the oven.

The high electromagnetic field strength associated with applying the full energy of the microwave oven, even for only a portion of a duty cycle, can cause lighting, standing waves, and hot spot problems when using microwave energy to polymerize dental articles such as dental prosthetics. When microwave energy is used to heat water or articles of food, for example, using the average power delivered to the target article is adequate to evaluate the energy absorption because the thermal and dielectric characteristics of the article are constant and relatively uniform. In contrast, when microwave energy is used to cure polymer dental articles the changing characteristics of the targeted article, both in terms of changes in the dielectric constant of the material that changes microwave energy absorption and in terms of changes in thermal conductivity that changes the manner in which thermal energy is translated throughout the article, make the use of average power delivered to the targeted article more complicated and less meaningful. The present invention recognizes this limitation of conventional commercial microwave ovens and solves these problems by creating a microwave polymerization system for dental articles utilizing metered and controlled microwave energy that is preferably continuous and voltage controlled, and regulates the application of this microwave energy by use of various feedback mechanisms.

Referring now to FIG. 1, one apparatus, provided in accordance with an extra-oral embodiment of this invention, comprises a microwave applicator having a three-dimensionally defined irradiation space having the format of a cavity (1), which is open at least on one side and includes a means of preventing the escape of microwave through the opening such as a door (2). The door has a means of being guided to a precise closing position such as hinges (3), and is able to be locked. The opening dimensions are preferably less than those of the walls of the cavity. The door is made of materials similar to those used for the cavity, being of good conductivity and dissipation for the electrical, thermal and microwave energy, including conductive metals or metal-plated materials. The dimensions of the cavity applicator and walls should preferably be set to minimize electromagnetic resonance or standing waves situations which may occur in some internal zones of the cavity applicator, thus causing hot or cold spots. Therefore, the dimensions of the cavity should not be a multiple of the wavelength $\lambda g$ of the transmitted microwave energy or pair fractions of the wavelength such as ¼, ½. For example, for the frequency of 2.45 Ghz, the wavelength is: $\lambda g=n/f=4.82$ inch; 9.64 is a multiple of $\lambda g$; 11.24 is a multiple $\lambda g/3$ and is not "resonant" and is preferred as a cavity wall dimension. A flat flange (4) made of said conductive materials is fixed to the opening of the cavity applicator, and extends outwardly from the walls, and comes into close contact with a wave trap (5), preferably mounted on the door, and which should have a dimension of $\lambda g/4$ of the emitted wave length. Leaky microwaves will be 90° out of phase when going outward as well as when returning, obliging the leaky waves to travel a total of 180°. The returning waves will be in counter phase with the leaking waves thus producing an energy cancellation. Each corner of the door is provided with a curved band (6) to maintain the said $\lambda g/4$ distance of the emitted wavelength, and the wave trap's efficiency. To minimize wave leakage, microwave-absorbing materials may also be installed in the wave trap. A means for efficiently locking the closed door is provided such as a T-screwing handle (7). Safety microswitches (8) are installed in a serial manner to electrically disconnect the microwave generator electrical supply when the door is open. A rectangular wave guide (9) or a cable, connects operatively the cavity applicator to the microwave source. The wave guide includes a means of being tuned (10), and in one preferred embodiment, comprise a directional coupler (11). An aperture (12) is made both in the wave guide and in a wall of the cavity, such that they are juxtaposed. This creates a passage for electromagnetic waves to enter the cavity. The aperture preferably has a length corresponding to $\lambda g/2$ of the employed wave length and a width equivalent to the wave guide width. A deflecting plate (13) is fixed at one end of the wave guide at an angle of about 45°, and causes the incident microwave beam to deviate into the cavity. The means of tuning the wave guide and system is advantageously provided on the wave guide.

For example, three holes can be drilled into one wall of the wave guide, and three tuning screws are placed into the threaded holes across the said wave guide wall, the space between the holes is preferably at a distance equivalent to $\lambda g/4$. This provides an efficient means to control and reduce the standing waves in the wave guide and the microwaves that are returning to the microwave source (14).

In one embodiment of the microwave applicator, a probe consisting of a directional coupler is mounted close to the output of the microwave source on the wave guide. This coupler senses the transmitted and reflected microwave magnitude and permit the monitoring and control of irradiation parameters. The directional coupler includes high frequency detecting diodes that are mounted on a printed circuit, which is mounted on the wave guide. The output of detecting diode optionally is connected to an electronic display to permit the irradiation monitoring and control of the transmitted and reflected microwave levels through the process in real time by an operator. Preferably, the microwave probe is connected to a central process micro controller to follow a preset or real time self-adjusted thermal processing program including irradiation modes and intensities based on desired curing times and the particular composition of the resin matrix to be cured. It will be seen that the measurement of the transmitted and reflected microwave energy allows for calculation of the actual microwave energy absorbed by the article being irradiated which can be monitored and adjusted as desired during the polymerization curing process.

Figure 2:
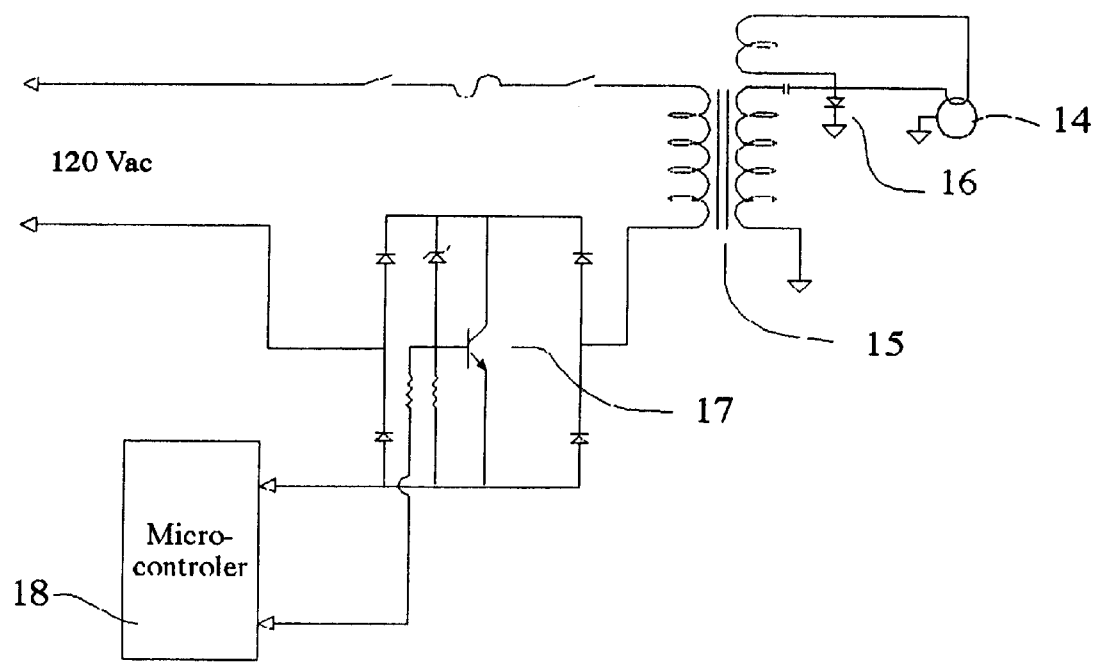
FIG. 2 is an electrical schematic of the control circuitry for generating the microwave energy in the microwave oven embodiment shown in FIG. 1.
Figure 4:
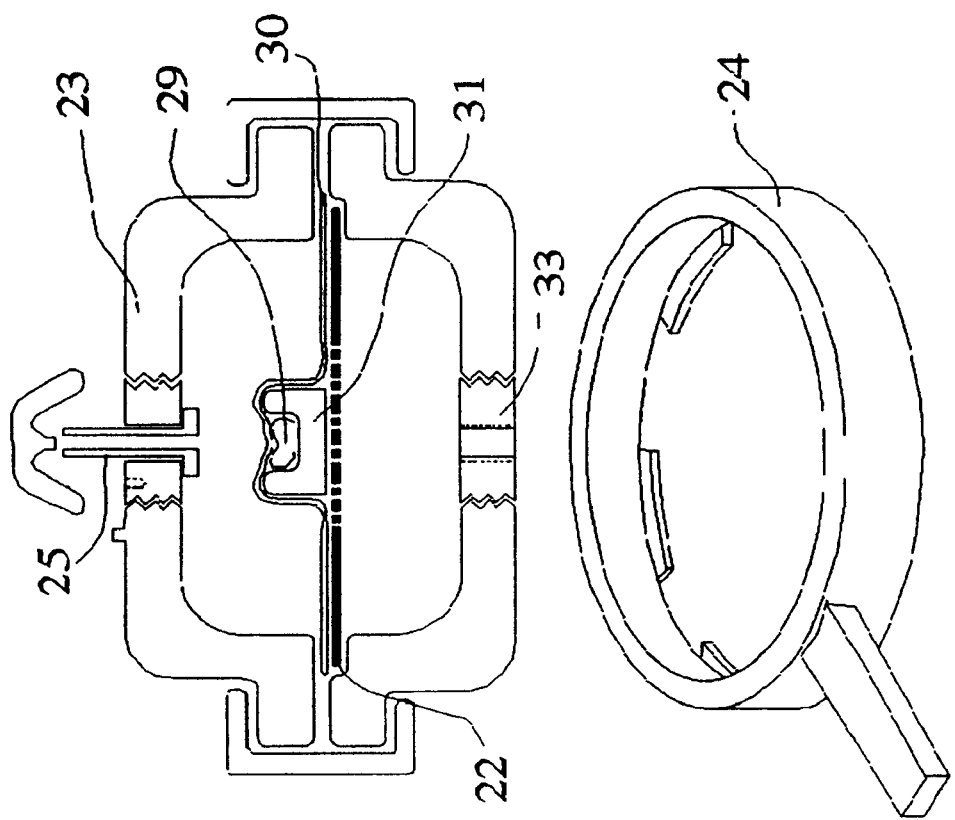
FIG. 4 is a cross-sectional side view of the flask shown in FIG. 3.
Figure 3:
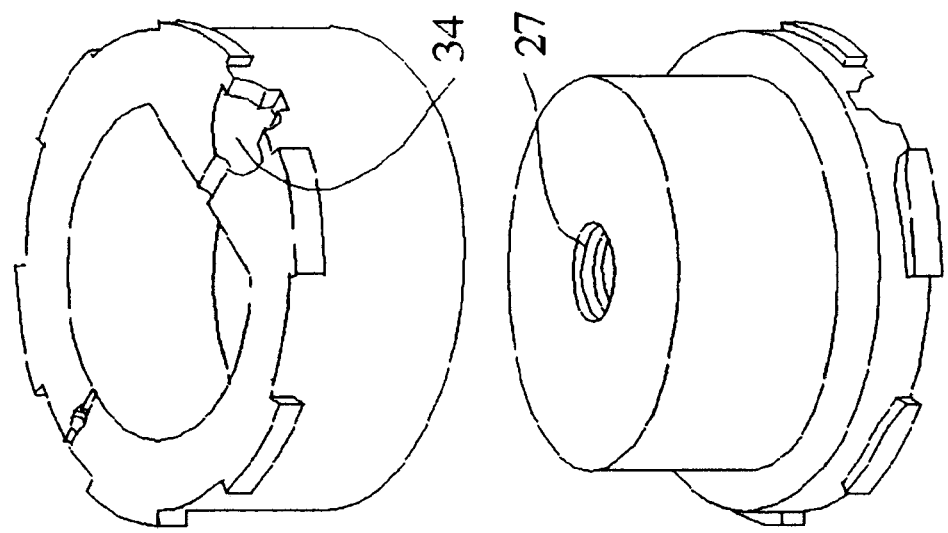
FIG. 3 is an exploded isometric view of a flask for use in the microwave oven embodiment shown in FIG. 1.

In one embodiment, as shown in FIG. 2, the control of the microwave generation is accomplished at the source by changing adequately the base voltage at the transistor, such as disclosed in diagram 1, for a precise control of the wave generator output power. For a microwave generator of 2.45 Ghz, such a magnetron, usually about −3500 DC volts are required to function. A high voltage transformer (15) raises the electrical voltage to about 1750 AC volts; then, a doubling circuit (16) composed of a high voltage condenser and a high voltage rectifying diode brings the voltage to about −3500 DC volts. A secondary low voltage coil of 3 AC volts supplies the heating filament of the mode of the microwave generator. The base of the transistor (17) is connected to a micro controller (18). This power transistor can be used as a variable resistor, to permit monitoring and automated management of the different irradiation and timing functions during the process. This providing permits the control of the microwave output power in two ways. First, by changing the duty cycles at the transformer by applying pulses to the base connection of the transistor. The second way of controlling of power is to reduce conveniently the applied voltage of the primary circuit of the transformer by changing adequately the base voltage of the transistor. This embodiment permits a soft management of microwave power by avoiding overheating of the microwave source, providing adequate heating of sensitive small sized or high absorbency materials, and avoiding the occurrence of corona discharges, particularly when metallic objects are used.

Referring again to FIG. 1, the generated microwave energy travels through the wave guide, is introduced and radiate into the defined exposure space from the wave guide aperture. To further reduce the standing wave patterns presence in the cavity application system, one or more microwave stirrers (19) are made with microwave deflecting blades and installed on an axle through a bushing on one or more of the cavity inside walls. The stirrer rotates by means such as a belt, pulleys, and electrical motor (20). The overall surface of the stirrer can be about ¾ of dimension of the cavity's wall. Each blade has a different configuration and passes close to the aperture causing the microwave beam to be oriented and delivered to different areas of the cavity. The materials used for the fabrication of the stirrer should have good electrical conductivity. The stirrer shaft is preferably made of a non-conductive material to minimize microwave conduction and leakage through the bushing. To improve the homogeneity of the established electromagnetic fields in the cavity microwave applicator, flat or curved reflectors made of conductive, specialty materials or active electromagnetic components may be fitted in appropriate locations such as at the lower corners useful to enhance energy distribution uniformity. The apparatus is provided with a stand (21) made of microwave transparent material to support suited dental compositions or objects that are to be microwave irradiated.

In one embodiment, as shown in FIGS. 3, 4, 5, and 6, in order to produce a dental polymer based object with high flexural strength and high modulus of elasticity and very low levels of post-cure leachables, being preformed or not, is irradiated and internally heated while compressed by a fluid such as air or nitrogen, resting on perforated tray (22) in a flask (23) made of heat and pressure resistant microwave partially transparent materials which may be filled and reinforced such as polyester, polyethylene, polypropylene and polysulfone, and having at least two body members and a means of clamping such as screws and, preferably, as the disclosed bracket (24) and a pressure limiting valve (25). When used in conjunction with the provided cavity applicator, the flask is introduced in the cavity and is connected to a mechanical gas coupling means (26) being positioned on a wall and or the bottom of the cavity applicator. This permits the introduction or removal of gas as needed before, while and after the irradiation of the processed target. A gas such as air or nitrogen is introduced through one of the flask pneumatic connections such as the ring opening (27) provided with each body member of the flask and allows easy and fast processing and making of objects having highly desirable properties. Preferably, a means of rotary mechanical gas coupling which employs an electrical motor (28), permit more uniform microwave exposure of the substance or object by entertaining the flask and targeted object in a rotary movement in the cavity while under pressure a constant. Microwave absorbing substances such as water can be introduced into the flask recess to increase heat or steam generation and the control and metering of the microwave can be adjusted to accommodate such a two-stage thermal transfer process.

In one embodiment, a means for a vacuum forming method is characterized by the use of the ring opening of the lower body member of the flask and a mechanical gas coupler which is positioned at the bottom of the cavity wall, in connection with a vacuum source to allow the thermal conditioning of thermoplastic softening compositions as well as the cure of thermosetting dental material compositions with highly desirable qualities useful in many dental applications, such as fabrication of dentures, trays or base plates, by attracting with suction the polymer-based material before and/or during the irradiation towards the mold, positioned on a dental model and a perforated tray to condition thermoplastic or thermohardening dental materials.

In one embodiment, the lower half of the flask is connected by providing coupling means to a vacuum source. A pasty polymer-based material (29) is set on or in a mold or pattern and positioned on a perforated tray in the flask. A flexible membrane (30), made of a material partially transparent to microwaves, such as silicone rubber, is firmly retained by a means such as a recess between the two body members of the flask, permitting the forming of a dental material by applying hydrostatic forces while microwave irradiated. Additional pressure can be exerted on the dental material by the introduction of pressurized gas from the upper ring opening of the flask. The embodiment is useful in the fabrication of dental devices such as tray, base plate, fiber reinforced composite crown and bridge, and molding of thermoplastic based objects such as vinyl esther oral protectors, permitting to reduce substantially the size and the number of the voids.

In one embodiment, a dental model (31) made of materials such as wax or elastomer, which can bear components such as artificial teeth, having the forms of the object to be produced is vested in a coating material (32) such as plaster in a flask having at least two body members and a clamping means. First, the cup-shaped recess of the lower member of the flask is filled with the coating material, then the model which may include a plaster cast is positioned in the coating material to a depth that is about half of its total height or to its largest contour. Once the coating material is set, a separating medium such as alginate based isolation solution for plaster is applied to its exposed surface. The two parts of the flask are then joined by a retaining and alignment setup such as screws and nuts and preferably clamping bracket means. The jointly clamped body members of the flask are then filled with more fluid coating material through its upper ring opening. Each ring opening (33) can be secured to the flask by means of threading or a shoulder. Once the added coating or mold making material is set, for dental patterns made of wax or the like, the complete flask is heated in the apparatus or in a hot water bath a few minutes to soften and melt the wax. Subsequently, the flask is split opened after removal of the clamping means, thus exposing the internal forms of the mold and defining the shape of the object to be produced as well as holding in position, objects such as artificial teeth. All of the parts are then washed with hot water. When using thermosetting material, an isolation medium is applied to all exposed surfaces of the mold to prevent the adhesion of the polymer material when in close contact with the mold at the processing stage. The fabrication method of the mold resembles to the known technique of lost wax casting. A drying treatment of the plaster molds can be done by its irradiation and heating in the cavity applicator or an oven. Once the dental mold is made, it is packed and may also be painted or sprayed by a dental material composition. The flask members are then clamped, introduced and mechanically connected in the cavity applicator to a fluid under pressure such as air and the process of microwave curing is initiated.

Figure 6:
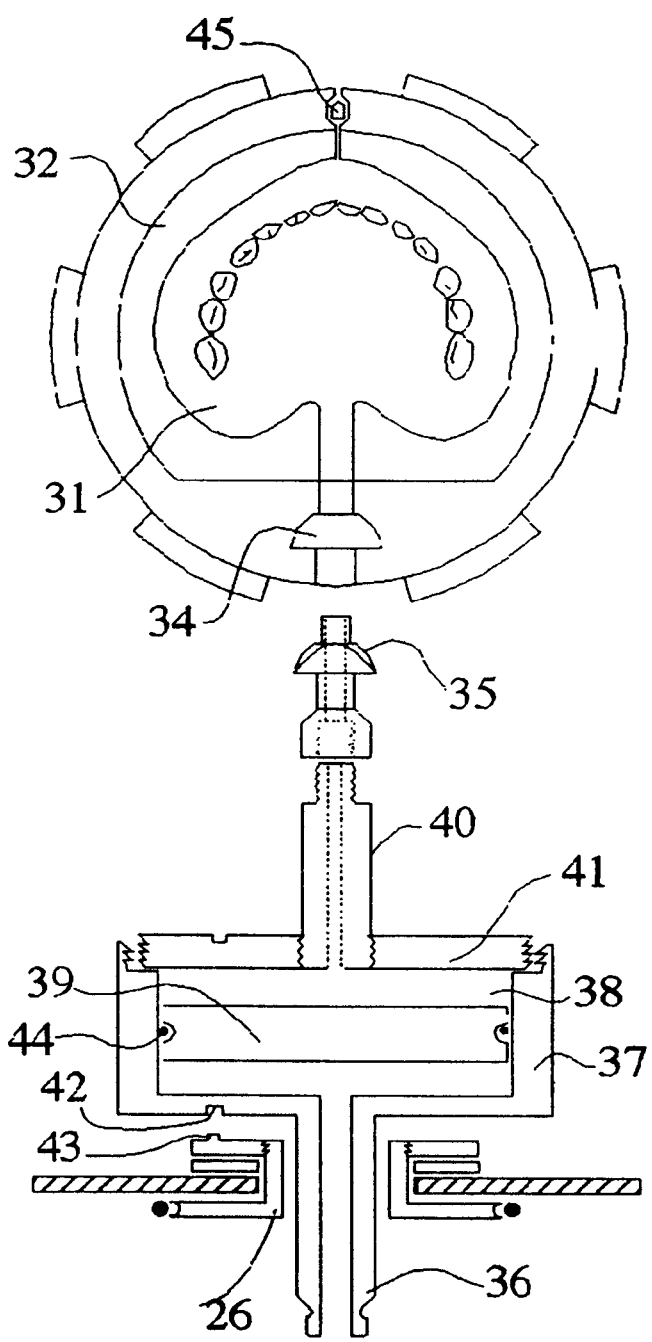
FIG. 6 is a partial cross-sectional side view of the flask of FIG. 3 in position in the microwave oven embodiment of FIG. 1.

In one embodiment, as shown in FIGS. 5 and 6, the flask is provided with an opening (34) preferably with the disclosed means of quick connection permitting the positioning and removal of the injection nozzle (35) while flask body members are joined. The mold space within the flask is operatively connected to the flask opening through vested runners made of material such as wax, preferably set on the model before the second filling of the flask of the coating material. Physical changes, including the progressive mold filling densification and the volumetric shrinkage of many thermally conditioned polymer-based materials, is substantially compensated in this invention with the pressurization and, when needed, introduction of the fluid polymer-based dental materials into the flask. The material injection means includes the use of a fluid conduct (36) with a male mechanical hydraulic coupler which allows the introduction of a fluid into the fluid conduct (37) through the mechanical coupler into the cavity applicator, which results in the compression filling of the materials contained in fluid dental material reservoir (38) into the mold. When under a hydraulic pressure, the piston (39) forces the material from its compartment through the injector (40) and the opening of the flask and to fill the mold. The cover (41) of the capsule is made to be removable by a means such as threads and is connected to one or more injectors in connection with the flask. The capsule can be advantageously trained into a rotary motion transmission by means such as a key path (42), on a rotary platform pin (43) in the cavity to enhance irradiation uniformity of the mold and dental composition while submitted to hydraulic forces. The piston and the capsule are advantageously equipped with scaling joints (44). For the processing of some materials such as thermo-hardening polymers, the capsule, conduct, and nozzle are preferably shielded by being made of microwave impervious materials such as steel, and conserve the unprocessed material compositions in its original temperature and fluidity condition, under pressure and while being continuously available and able to be introduced as needed in the mold to compensate for the volumetric shrinkage and to fill voids and/or compensate for progressively occurring deformations of the object in thermal process. This continual pressurized injection allows a substantial increase of the dimensional precision of the produced dental objects. The presence of porosity is significantly reduced and produced objects are more suited for dental uses in terms of biofunctionality, fit and durability when compared to objects such as prosthetics produced by the conventional methods and materials. Preferably, a bleeder (45) made of microwave transparent materials is employed in an appropriate housing made on at least one of the flask members closing surface, and provides a means of hydraulically connecting the mold to the exterior of the flask, useful in reducing the energy and time required to appropriately fill the mold and also minimize porosity occurrence. Said bleeder accelerates the emptying of the existing air in the mold space when introducing resinous materials into it while preventing the leakage of resinous fluid dental materials under pressure by moving outwardly and blocking the external orifice of the housing.

In one embodiment, low microwave absorbing materials including thermoplastic resins are indirectly heated with the use of a compression-injection capsule coated or layered with microwave absorbing substances such as metal oxides including zinc oxide, carbon black and specialty ceramics.

Figure 8:
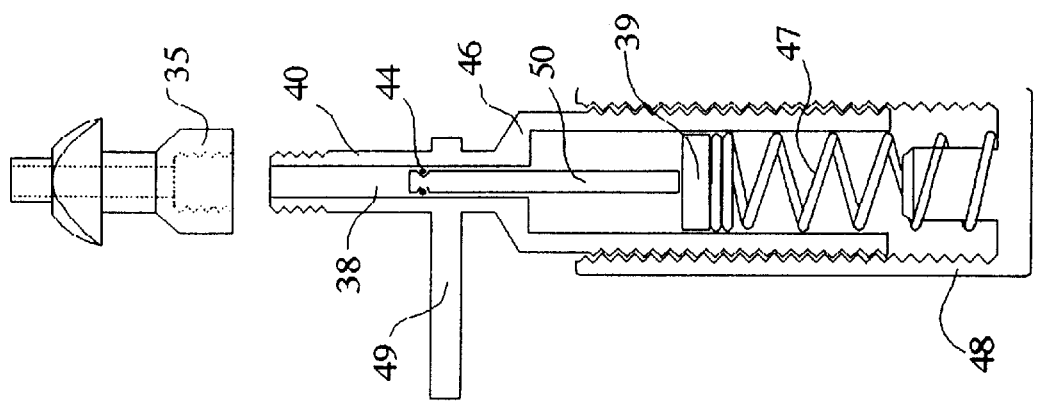
FIG. 8 is a partial cross-sectional side view showing the details of a preferred embodiment of the polymer material injector system of the microwave oven embodiment of FIG. 1.

In one embodiment, as shown in FIG. 8, an economic manual fluid resin pressurization and injection device (46) is provided to remove the need of being connected to an external pressurized fluid source. A mechanical force accumulator such as a spring (47) is compressed by turning the internally threaded cylinder (48) while holding the device handle (49). A force boosting piston (50) is especially useful for molding and filling of composite curable dental materials. The injection nozzle and the piston acts as previously described. This embodiment can be used with the disclosed cavity applicator and flask or miniaturized, and employed with the hand-held intra-oral microwave applicator.

In one embodiment, a shielded temperature probe made, for example, of a thermocouple with a temperature dependent resistor, a fluoro-optic, or an infrared temperature magnitude detecting means is advantageously used with a pivoting electrical connector to permit the sensing of the thermal conditions of the microwave irradiated target. This embodiment permits a precise setting of the pace of thermal conditioning as well as the indication of the reach of a specific temperature magnitude useful for the thermal processing of delicate materials such as some thermoplastics or low temperature boiling monomers, as well as to increase safety in the dental prosthesis sterilization functions and is preferably used in connection with the central micro-programmable controller to optimize the feedback and control of the microwave generator.

Figure 7:
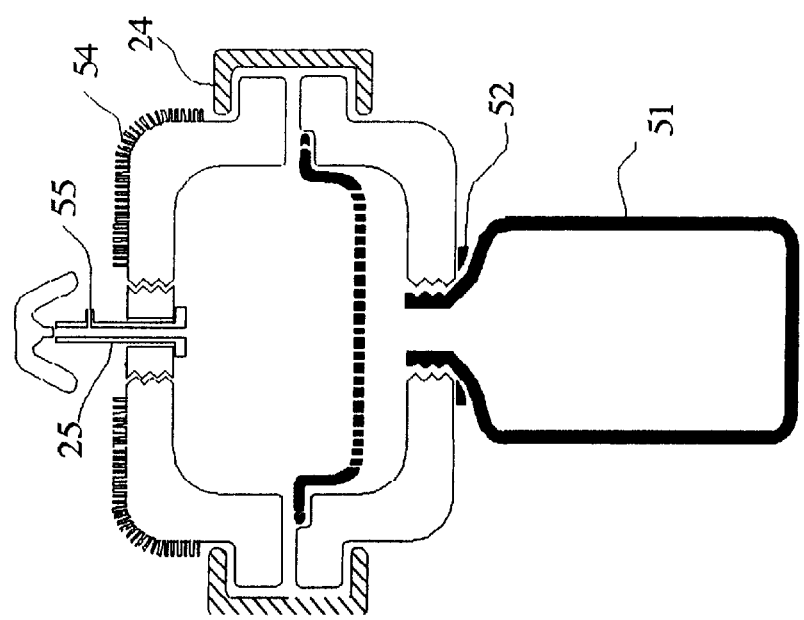
FIG. 7 is a partial cross-sectional side view of the flask similar to FIG. 6 showing the details of a preferred embodiment of the air pressurization system.

In one embodiment, as shown in FIG. 7, to permit a safe and quick sterilization of dental objects without fear of corrosion or arc occurrence, a cylindrical column (51) made of microwave transparent materials is closed at one end and externally threaded at the neck, is made of sufficiently thick glass or polymer to resist heat and pressure, and is used in conjunction with the provided flask and cavity applicator. The cylindrical column permits heating of a liquid and hot steam generation and, optionally, the production of a microwave shielding atmosphere is screwed into the lower flask half member through its ring opening with its sealing joints (52). A liquid such as distilled water is introduced to fill the column up to a pre-determined level. A specially shielded flask operatively connected or not with the steam generation column is introduced in the said cavity through the door, or only its column introduced from the provided top circular opening (53) into the cavity applicator, which is provided with a disk form closing door. To sterilize, the steam, having reached the evaporation temperature under microwave irradiation, fills the flask with the vapor rise up. The upper flask half is preferably made of a heat conduction and exchanging material (54) such as stainless steel and comprises a heat sink to cool by conduction the internally contacting warm vapor. The condensed and liquefied sterilizing solution returns by gravity to the base of the column where it is repeatedly heated and evaporated, providing a constant steam flow and contact with treated dental objects contained in the flask. To detect the temperature magnitude with high accuracy, the temperature probe for a microwave environment can be placed within the flask. The flask can be sealed immediately following removal of the probe after sterilization with the use of an annular elastic sealing coupler positioned on one of the flask inlets, such as the injection opening or the pressure limiting valve manifold. The means of microwave and temperature magnitude detection permit a precise control and delivery of microwave to a dental target, useful in avoiding arcing occurrence by generating adequate microwave power levels and/or creating a shielding vapor pressure atmosphere inside the flask. The temperature and microwave sensing and control are preferably done in an automated manner with the programmable micro-controller. Once the predetermined temperature is reached, a signal is sent to the micro-controller, which then reduces the power of emission so as to maintain a sufficient amount of time to sterilize (6 min). Equilibrium temperature is reached quickly since there are no great swings in the temperature and optimal control of the microwave delivery is achieved.

In one embodiment, the temperature is safely and economically controlled for sterilization function through a gas pressure sensor which is connected to the flask for example through the pressure limiter manifold (55) or vent to control the sterilization temperature inside the flask, specially when used with the shielded flask, positioned externally with only its steam column introduced in the cavity applicator. This pressure sensor is operatively connected to a micro-controller to maintain the right warm steam pressure temperature magnitude and permit monitoring. The temperature sensor for microwave environment can also, alone or jointly with the pressure sensor, be used with the disclosed device. Any increase of temperature of a gas having a given volume conduct to an increase of its pressure. By limiting and/or controlling the pressure of the gas, an effective control of flask internal temperature is achieved. The micro-controller controls the flask internal temperature via the microwave generator, using the provided microwave power control.

We have conducted complex dielectric permittivity, temperature and distribution pattern studies of microwave heated teeth and simulations of specific absorption rate distribution. The complex permittivity was measured on different types of dental tissues, using extracted teeth, including enamel, dentin and caries. Reflective coefficients have been obtained using a network analyzer. The characteristics of enamel caries and dentin are different. The dielectric loss factor of caries is fairly higher than that of normal healthy parts particularly in the millimetric wave in the frequency between 12 GHz to 25 GHz. When the tooth is exposed to millimetric microwaves in this range, caries are preferentially heated. Temperature rise can kill the microorganisms in caries. Control and/or extinction of microorganisms slow or stop the progress of caries, permitting previously carious tissue to recalcify by biological latent support of the pulp. Temperature distribution measurement with microwave heating reveals that the temperature of caries is higher than that of normal tooth tissue. These properties are used with the provisions of this invention for the diagnostic and treatment of teeth having caries and subsequent internal heat conditioning and/or curing of provided dental restorative materials. When dielectric loss factor is higher, the absorption of microwave is better and local temperature is higher. Microwave energy heats by radiation and is able to penetrate through various substances including desiccated tissue and thus, can create an addressed effect.

In general, various polymer-based material compositions are useful for the construction of dental devices. These compositions may be used in the filling of teeth and the construction of appliances used for replacing teeth and other oral structures. One utility of these compositions is in the construction and repair of removable dental devices such as dentures and dental anchored restorations such as crowns, bridges, inlays, and veneers. Also, utility is found in the making of mouth guards, oral border molding, impression trays, base plates, and orthodontic dental appliances. Various thermoplastic containing dental compounds are also advantageously thermally conditioned and softened while treated with the provided method and apparatus and formed subsequently by various methods.

One preferred composition for dental composites suited to be formed and hardened in accordance with the providing of this invention, consists of a polymerizable mixture including one or a selection from the large family of polyfunctional methacrylate esters, and oligomers including the compound prepared from one molecule of bisphenol A and two molecules of glycidyl methacrylate called 2,2bis[4(2-hydroxy-3 methacryloyloxy-propyloxy)-phenyl] propane, known as Bis-GMA for its lower degree of shrinkage, and/or 2,2-bis [4-methacryloxyethoxy)Phenyl] propane for its good water resistance properties. Other monomers, such as triethyleneglycol dimethacrylate for viscosity reduction, urethane dimethacrylates, spiro orthocarbontes, etc., are advantageously employed in admixture with silanized inorganic fillers and organic fillers, coupling agents, microwave-sensitive cure initiation system including organic peroxides and amines and color pigments are advantageously added. The weight of the fillers as an overall weight of the composite is preferably in the range of 30 to 90% and include silanized silicon dioxide particles.

In one embodiment, compositions especially suitable for making dental removable appliances, such as dentures, is provided which comprise a liquid and a powdery component. The liquid component in accordance with the invention contains preferably from 40% to 90% of mono-, di-, tri-, or multi-functional acrylic monomer, a cross-linking agent, a plasticizer, a stabilizer, an accelerator and color pigments. The mono-, di-, tri-, or multi-functional acrylic monomer in accordance with the invention is within the scope of the formula:

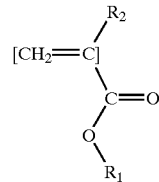

where R1, in accordance with the invention, is hydrogen, alkyl, substituted alkyl group, cyclic hydrocarbon, benzyl, ether, hydroxyalkyl, and R2 is hydrogen, halogen, alkyl, substituted alkyl or cyclic hydrocarbon group.

Monomers within the scope of the following formula are also particularly suitable to the invention:

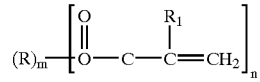

where R is an acrylic-free organic moiety, $R_1$ is hydrogen, hologen, halogen, alkyl, substituted alkyl or cyano radical, and n is an integer from 1 to 20 and m is an integer from 1 to 1000. These monomers may be used alone or in admixture.

The microwave-sensitive initiators in accordance with the invention include benzoyl and peroxide, dilauroyl peroxide up to 2,5%. The polymerization accelerator in accordance with the invention is a quaternary ammonium chloride, which is easily soluble in the methacrylate monomers and reacts with barbituric acid derivatives. A preferred compounds are the quaternary ammonium with an alkyl of 1 to 20 carbons, such as, dodecyltrimethylammonium. These quaternary ammonium chlorides may be added in alone or in admixture from 0,09 to 1,5%. The cross-linking agent, in accordance with the provided microwave hardening material compositions, is a polyfunctional monomer wherein at least two carbon—carbon double bonds, such as 1,3-butanediol dimethacrylate, 1,4-butanediol dimethacrylate, 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate, pentaerythritol tetraacrylate, trimetylolpropane triacrylate. The cross-linking agents may be used alone or in admixture.

Polymerization promoters for the monomers of the provided curable material compositions for the present invention are useful because they rapidly react with the quaternary ammonium chloride to produce radicals, which promotes a rapid and uniform polymerization in the composition and a higher degree of conversion. The barbituric acid derivative, in accordance with the invention, includes 1,3,5-trimethylbarbituric acid, 1,3-dimethyl-5-isobutylbarbituric acid, 1,3-dimethyl-5-phenylbarbituric acid, 5-n-butylbarbituric acid, 5-ethylbarbituric acid, 1-cyclohexyl-5-ethylbarbituric acid, and 1-benzyl-5-phenylbarbituric acid.

These acid derivatives may be used alone or in admixture in very small amounts. The polymerization stabilizers comprise hydroquinone, hydroquinone monomethyl ether or 4-ethoxyphenol, which are usually added to the liquid component of dental compositions (up to 4%). The plasticizer, in accordance with the invention, is generally a low molecular weight ester, such as dibutyl phthalate or phosphates.

The composition for a one component microwavable curable material system, in accordance with this invention, is approximately the same as the one for the two component materials with some variations mainly in the initiation system. Preferred initiators for a one component dental composition for denture or such need to be thermally stable at room or higher temperatures such as 50° C. and initiate polymerization at higher temperatures such as benzopinacole, tert-butyleperbenzoate, and 2,2'dichlorobenzopinacol.

The powder component in accordance with the invention includes from 20% to 80% of mono-, di-, tri-, or multi-functional acrylic or acrylate ester polymer. The powder may advantageously include from 5% to 40% of a copolymer. The powder component, in accordance with the invention, may advantageously include from 0,1% to 3% of an initiator for radical polymerization including organic peroxides such as benzoyl peroxide and dilauroyl peroxide. The powder component, in accordance with the invention, can include up to 1% of a barbituric acid derivative to promote chemical reaction. The mono-, di-, tri-, or multi-functional acrylic polymer used in denture base in accordance with the invention are:

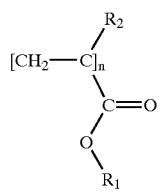

where the R1, in accordance with the invention, is hydrogen, alkyl, substituted alkyl group, cyclic hydrocarbon, benzyl, ether, hydroxyalkyl, R2 is hydrogen, halogen, alkyl, substituted alkyl group, and n is an integer at least equal to 2. The copolymer in accordance with this invention are mainly composed of methyl methacrylate polymer or a mixture of methyl methacrylate polymer and an methacrylate polymer other than methyl methacrylate polymer.

Inorganic and organic fillers may be added into the compositions of one or two components denture base. Useful inorganic fillers include glass, metal ceramics, silicon dioxide, in powdery or fiber format, which are preferably silanized with a coupling agent, such as 3-methacryloxloxypropyltrimethoxy. Organic fillers include splinter or bead polymers of high molecular weight, or fibers such as aramide fibers, polyacrylate fibers, polyamide fibers, and polyacrylonitrile fibers. Organic fillers may be used alone or mixed with inorganic fillers.

Another example of polymers used in the dental arts is soft liners. A permanent soft liner is placed on the interface between the interior surfaces of the denture and the denture-bearing mucosa of the patients. This soft liner should be permanently resilient, highly stable in dimension, adhering to the denture-base polymer, biocompatible, easy to clean and not capable of sustaining microbial growth. Several kinds of soft liners including polysiloxane, polyurethanes, plasticized polymethacrylates, polyvinyl chlorides and polyphosphazene fluoroelastromers are currently employed.

Most soft liners do not fulfill the above requirements due to inherent disadvantages. These include the leaching of potentially harmful bonding agents, such as epoxy and urethane adhesives, sulfuric, perfluoroacetic acid, poor adhesion to the polymethylmethacrylate (PMMA) denture base material, porosity in denture base and the liner resulting from vaporization of the incorporated monomers and solvents, dimensional changes caused by micro-shrinkage and dehydration and rehydration steps. The improvements of denture soft liners may be based on the use of novel materials, such as methacryloxy polydimethylsiloxanes or methacryloxyalkyl-terminated polydialkylsiloxanes.

Microwave curing resilient compounds for making devices such as denture liners are molded and cured with the provided novel method and apparatus including organopolysiloxanes and phosphonitrilic fluoroelastomers [poly (fluroalkoxy)phosphazene] with a cross-linking agent, a filler and an initiator. Silicones are containing a repeating silicone-oxygen backbone with organic side groups attached via carbon silicone bonds. One composition for soft denture liners, in accordance with this invention, contain silicones within the scope of the structural formula:

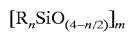

Wherein n–1–3 and m>1. R groups are usually methyl, longer alkyl, fluoroalkyl, phenyl, vinyl, alkoxy or alkylamino. One preferred silicone compound is polydimethylsiloxane (PDMS) of the following structure:

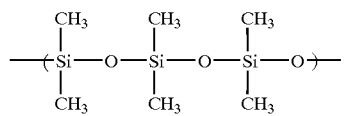

Methacryloxy-terminated polydimethylsiloxanes are particularly useful since they bond well to PMMA made dentures due to the chemical similarity.

The cross-linking agents for soft liners are normal multi-functional monomers wherein there are at least two carbon—carbon double bonds. Preferred cross-linking monomers are acryloxy or methacryloxyalkyl-terminated siloxane monomers, such as 1,3-bis[(p-acryloxymethy) phenethyl] tetramethyldisiloxane, 1,3-bis(3-methacryloxypropyl) tetramethyldisiloxane, due to chemical similarity.

The normal initiators in the soft denture liners in accordance with the invention are general peroxides, such as benzoyl peroxide, lauroyl peroxide, which are usually added to the powdery component of resilient compositions in small amounts.

The phosphonitrilic fluoroelastomers (poly(fluoroalkoxy) phosphazenes) in accordance with this invention are polymerized by monomers within the following formula:

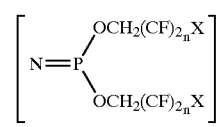

where X is H or F, and n is usually from 1 to 11, 30 to 60% of total ingredients for a firmer liner and up to 90% for a softer one.

The cross-linking agent suitable for the fluoroelastomers are monomers with at least two functional groups, such as tetraethylene glycol dimethacrylate, ethylene glycol dimethacrylate, 1,6-hexamethylene glycol dimethacrylate, trimethylopropane trimethacrylate, pentaerythritol triacrylate, pentaerythritol triallyl ether, pentaerythritol tetraacrylate.

The fillers, which are preferably mainly hydrophobic, improve hardness and the ability to grind and polish the cured resilient materials and the bond durability between the liner and base. Particles of fillers may be beads or fibers, pigments and other additives can be added to the soft material system (fillers 7% for soft, 30% for firm liners).

Thermoplastic compounds such as polyfunctional methacrylate, polycarbonate, polysulfone, fluoropolymers, elastomers, polyurethanes, impression compound, wax, polycaprolactone and mixture of thermoset and thermoplastics are advantageously heat processed with the provided method and permit dental rehabilitation.

Microwave absorbing substances can advantageously be incorporated into disclosed thermoplastic and thermohardening material compositions to decrease internal heat generation of compositions which does not have sufficient dielectrical loss when microwaved, nor do they have sufficient heatability for a desired speed of heating. These microwave absorbents are also useful when the employed polymeric material has only a low microwave absorption behavior at low temperatures such as many thermoplastic polymers including polycarbonate and also for substantially increasing the speed and the addressability, such as in welding and joining functions. These absorbers may be powdery, hollowed, coated and comprise ferromagnetics, metallic oxides, or specialty ceramics. Microwave absorbent materials and/or sterilants can be advantageously utilized with the intra-oral embodiment of the present invention to increase the speed and addressability of heating the dental composite and to increase the effectiveness of the sterilization of the targeted caries.

The following tables set forth several examples in accordance with the various aspects of the present invention. All ratio for materials are expressed in weight.

EXAMPLES

| Cavity applicator dimensions | | | |
|---|---|---|---|
| Cavity: | 32 cm × 32 cm × 28 cm made of steel | | |
| Wave guide: | 3.8 cm × 7.6 cm × 45.7 cm such as WR 284 made of copper | | |
| Steerer: | 20 cm made of steel | | |
| Flask (made of polypropylene) | | | |
| diameter interior: | 8 cm | bleeder 2 mm diameter: 3.5 mm long | |
| diameter exterior: | 13 cm | membrane thickness: 3 mm | |
| recess depth: | 1.5 cm | ring: 3.5 cm | |
| Injection capsule dimensions (made of stainless steel/wall thickness 6 mm) | | | |
|  | Diameter | Stroke | Piston height |
| Dentures: | 10 cm | 5 cm | 2 cm |
| Manual: | 5 cm | 6 cm | 2 cm |
| Composite boosting piston: | 3.5 cm | 2.5 cm | 1.5 cm |
| Process programmable micro-controller | | | |
| Micro-controller Pic of Microship inc. or Parallax | | | |
| Microwave frequency | | | |
| Magnetron frequency: | 2.45 GHz | Output power 600 W | |
| Impatt diode frequency: | 24 GHz | Output power 5 W | |
| Vacuum source such as a 600 W cleaning aspirator for dental | | | |
| Vacuum forming of resinous or microwave softened dental materials | | | |
| The steam generation column is made of polycarbonate with walls having a thickness of 1 cm | | | |
| 6 cm inside diameter and a height of 12 cm | | | |
| Pressure limiting valve | | | |
| Aperture: | 4 mm$^2$ | | |
| Weight: | 80 g | | |
| Pressure: | 24 PSI | | |

| Experiment of decay control in the cavity microwave applicator | | | | |
|---|---|---|---|---|
|  | Preparation | Microwave irradiation | Incubation | Results |
| Section of decayous freshly extracted human teeth prepared, 2 mm$^3$ | Surface disinfection, 15 seconds steeping in cloramine T solution | 1.5 W/cm$^2$ energy density of irradiation (200 W in the cavity applicator) 60 sec. | Culture of irradiated & non irradiated witness decayous teeth sections in a medium at 37° C. 24 h. | Microwave irradiation destroy 80% carious zone microorganisms Witness teeth cultures cloudy |

-continued

Examples of microwave processing of polymer based material

| | Steps of the procedure in order | | |
|---|---|---|---|
| | Compression, forming | Microwave irradiation | Bench cooling |

Aesthetic composite

| A 100 de 3M inc, color ivory, 0.15% of benzoide peroxide for initiation. 1 cc | | | | |
|---|---|---|---|---|
| | Example 1 | 1 min | 3 min, 450 W | 3 min |
| | * Example 2 | 2 min | 5 min, 250 W | 3 min |
| * Mechanical test (3 points bend, failure) of specimens of example 2 | | Size: 25 × 2 × 1.75 mm | Load at max | Displacement at max |
| Testing specifications, crosshead speed 2 mmm/min, Instron device | | 25 PSI membrane compression, flask & plaster mold | 45 N | 0.42 mm |

| | Mold injection filling | Microwave irradiation | Bench cooling |
|---|---|---|---|
| GC Acron resine for dentures, 40 cc Flask with bleeder plaster mold Large capsule | Example 1  100 psi, 3 min | 7 min,. 225 W + 1 min, 400 W | 6 min |
| | Example 2  100 psi, 3 min | 4 min, 450 W | 6 min |
| Soft materials Molloplast B, Regnesi & co GER, 40 cc | 80 psi, 5 min | 12 min, 225 W + 1.5 min, 400 W | 6 min |

Examples of some polymer based dental materials processed with the providing of this invention

| | Step 1 Compression forming | Step 2 Microwave irradiation |
|---|---|---|
| Composite resin matrix BisGMA - TEDGMA - Ratio 6/4 0.5% of benzoide peroxide for initiation | 15 PSI | 20 PSI |
| Example | 2 min | 5 min 350 W |

Disq size 6 mm diam.X3mm., plaster & Teflon mold: diametral compression strength 100 MPa, 80 degree of conversion
ADA specification no. 27

| | Filling a denture plaster mold within the flask | Microwave irradiation |
|---|---|---|
| GC Acron resine for dentures, 40 cc Flask with bleeder plaster mold Large injection capsula | Example  55 Kgf/cm² 3 min | 30 Kgf/cm² 6 min,. 300 W |
| Soft materials for denture base lining Molloplast B, Regnesi & co GER, 40 cc Large injection capsula | mold filling 45 Kgf/cm², 5 min | 5 min, 375 W, 20 Kgf/cm² |

Repair, soldering of denture resin

| G-C ACRON, denture repair material powder & fluid | ~25 psi, air pressure - 80 g pressure limiting valve weight on a regular dental index made of plaster 2 min, 200 W + 1 min, 350 W |
|---|---|

Repair of denture resin

| G-C ACRON, denture repair material powder & fluid | 18 psi, air pressure - on a regular dental index made of plaster 5 min, 325 W |
|---|---|

| Microwave softening of thermoplastic dental material | Microwave irradiation | Adaptation time |
|---|---|---|
| Border molding compound in a 5 cc syringe | 4 min, 200 W | 2 min |
| Dental custom tray, polycapratone sheet thermosoftening Thickness: 3 mm | 2 min, 300 W | 1.5 min |

| Microwave softening of thermoplastic dental polymers | Microwave irradiation |
|---|---|
| Border molding compound 5 cm³ plastic cylinder | 4 min, 200 W |
| Dental custom tray 3 mm, polycaprolactone sheet | 2 min, 300 W |

What is claimed:

1. A microwave polymerization system for polymerizing dental prosthetics and dental composites formed of a resin matrix comprising:
   a source of microwave energy;
   an antenna defining a space during an application of microwave energy to the resin matrix that is in the form of a cavity, defined by continuous walls having at least one opening therein to permit insertion and removal of at least one flask containing a dental prosthetic made of a resin matrix that is to be microwave polymerized;
   a wave guide connected to the source of microwave energy and to the antenna to deliver microwave energy to the antenna;
   a gas pressurization system operably coupled to the flask that applies a pressurized gas to the flask during the application of microwave energy; and
   a material injection system that introduces additional resin matrix into the flask during the application of microwave energy.

2. The microwave polymerization system of claim 1, further comprising means for rotating the flask within the cavity and including rotatable couplers for connecting the gas pressurization system and the material injection system to the flask.

3. The microwave polymerization of claim 1, wherein the material injection system comprises:
   an injection nozzle operably coupled to the flask that introduces additional resin matrix into the flask during the application of microwave energy; and
   a piston under a hydraulic pressure operably forcing additional fluid resin matrix from its compartment through the injection nozzle.

4. The microwave polymerization system of claim 3, wherein the injection nozzle includes a means for quick connection of the injection nozzle with the flask.

5. A method of polymerizing dental prosthetics and dental composites formed of a resin matrix comprising:
   providing a source of microwave energy;
   applying the microwave energy through an antenna to the resin matrix;
   applying a pressurized gas to the resin matrix during the step of applying the microwave energy; and
   introducing additional material to the resin matrix during the step of applying the microwave energy.

6. A method of polymerizing dental prosthetics and dental composites formed of a resin matrix comprising:
   providing a source of microwave energy;
   applying the microwave energy through an antenna to the resin matrix; and
   introducing additional material to the resin matrix during the step of applying the microwave energy.

7. The method of claim 6, further comprising the step of applying a pressurized gas to the resin matrix during the step of applying the microwave energy.

8. A microwave polymerization system for polymerizing dental prosthetics and dental composites formed of a resin matrix comprising:
   a source of microwave energy;
   an antenna defining a space during an application of microwave energy to the resin matrix that is in the form of a cavity, defined by continuous walls having at least one opening therein to permit insertion and removal of at least one flask containing a dental prosthetic made of a resin matrix that is to be microwave polymerized;
   a wave guide connected to the source of microwave energy and to the antenna to deliver microwave energy to the antenna; and
   a material injection system operably coupled to the flask that introduces additional resin matrix into the flask during the application of microwave energy.

9. The microwave polymerization system of claim 8, further comprising means for rotating the flask within the cavity and including rotatable couplers for connecting the material injection system to the flask.

10. The microwave polymerization system of claim 8, wherein the material injection system comprises:
    an injection nozzle operably coupled to the flask that introduces additional resin matrix into the flask during the application of microwave energy; and
    a piston under a hydraulic pressure operably forcing additional fluid resin matrix from its compartment through the injection nozzle.

11. The material injection system of claim 10, wherein the injection nozzle includes a means for quick connection of the injection nozzle with the flask.

* * * * *